(12) United States Patent
Mukkalil et al.

(10) Patent No.: US 9,115,012 B2
(45) Date of Patent: *Aug. 25, 2015

(54) METHOD OF IMPROVING THE WATER QUALITY IN AQUATIC ECOSYSTEMS

(71) Applicants: Rajalekshmi Mukkalil, Cochin (IN);
Sripathy Ravichandran, Korattur (IN);
Haridasan Chirakkal, Chennai (IN)

(72) Inventors: Rajalekshmi Mukkalil, Cochin (IN);
Sripathy Ravichandran, Korattur (IN);
Haridasan Chirakkal, Chennai (IN)

(73) Assignee: Kemin Industries, Inc., Des Moines, IA (US)

( * ) Notice: Subject to any disclaimer, the term of this patent is extended or adjusted under 35 U.S.C. 154(b) by 18 days.

This patent is subject to a terminal disclaimer.

(21) Appl. No.: 13/724,994

(22) Filed: Dec. 21, 2012

(65) Prior Publication Data

US 2013/0193082 A1 Aug. 1, 2013

Related U.S. Application Data

(62) Division of application No. 13/027,382, filed on Feb. 15, 2011, now Pat. No. 8,367,125.

(60) Provisional application No. 61/304,942, filed on Feb. 16, 2010.

(51) Int. Cl.
*A01N 65/00* (2009.01)
*C02F 1/50* (2006.01)
*A61K 36/00* (2006.01)
*A01N 65/08* (2009.01)

(52) U.S. Cl.
CPC . *C02F 1/50* (2013.01); *A01N 65/08* (2013.01); *A61K 36/00* (2013.01)

(58) Field of Classification Search
CPC ..................................................... A61K 36/00
USPC .......................................................... 424/725
See application file for complete search history.

(56) References Cited

U.S. PATENT DOCUMENTS

| | | | |
|---|---|---|---|
| 3,446,733 A | 5/1969 | Shell | |
| 4,012,320 A | 3/1977 | Conner et al. | |
| 4,065,386 A | 12/1977 | Rigby | |
| 4,331,681 A | 5/1982 | Gutman | |
| 4,336,054 A | 6/1982 | Sjoerdsma | |
| 5,981,435 A | 11/1999 | Michelotti et al. | |
| 6,878,373 B2 | 4/2005 | Keeton et al. | |
| 6,966,982 B1 | 11/2005 | Chang | |
| 7,407,652 B2 | 8/2008 | Elston et al. | |
| 2006/0275324 A1 | 12/2006 | Elston et al. | |
| 2008/0210632 A1 | 9/2008 | Kruse | |
| 2009/0099135 A1 | 4/2009 | Enan | |

FOREIGN PATENT DOCUMENTS

EP 0896792 A1 2/1999

OTHER PUBLICATIONS

Huijun, Ding et. al., "Effects of two kinds of phenolic allelochemicals on the growth of *Microcystis aeruginosa*", "Environmental Science and Technology", Jul. 31, 2007, vol. 30, No. 7, Published in: China.
Weidong, Yang et. al., "Study on Growth of *Microcystic aeruginosa* Affected by Phenolic Allelochemicals", "China Environmental Science", Dec. 31, 2005, vol. 25, No. 4.
Wenyu, Han, "Identification of Methicillin-resistant *Staphylococcus* and Screening of Herbal Antibacterial Agents", "Medical Science & Technology Edition of Chinese Excellent MA Degree Thesis Fulltext Database, No. 4", Sep. 12, 2007.
Verschuere, L., Rombaut, G., Sorgeloos, P. and Verstraete, W. Probiotic Bacteria as Biological Control Agents in Aquaculture, Dec. 2000, Microbiology and Molecular Biology Reviews, 64 (4): 655-671.
Ridge, I. and Pillinger, J.M., Towards Understanding the Nature of Algal Inhibitors from Barley Straw, 1996, Hydrobiologia 340: 301-305.
Everall, N.C. and Lees, D.R., Use of Barley-Straw to control general and blue-green algal growth in a Derbyshire reservoir, 1996, Water Research, vol. 30, No. 2: 269-276.
Leu, E. Drieger-Liszakay, A. , Goussias, C. and Gross E. M., Polyphenolic allelochemicals from aquatic angiosperm *Myriophullum spiacaturn* inhibit photosystem II, 2002, Plant Physiology., vol. 130, No. 4, pp. 2011-2018.

*Primary Examiner* — Michael Meller
(74) *Attorney, Agent, or Firm* — Davis, Brown, Koehn, Shors & Roberts, P.C.; Kent A. Herink (57) ABSTRACT

A method for improving water quality in aquatic ecosystems is described. An effective amount of *Quercus infectoria* nut gall powder is added to the ecosystem to prevent excessive proliferation of pathogenic bacterial species thereby improving the health of aquaculture species in the ecosystem.

2 Claims, 4 Drawing Sheets

METHOD OF IMPROVING THE WATER QUALITY IN AQUATIC ECOSYSTEMS

This application claims priority to U.S. patent application Ser. No. 61/304,942, filed Feb. 16, 2010 and U.S. patent application Ser. No. 13/027,382, filed on Feb. 15, 2011, which is incorporated herein in its entirety by this reference.

The invention is related generally to water quality and, more specifically, to the application of an extract/powder from *Quercus infectoria* nut galls for improving the physical, chemical and microbiological status of water in aquatic ecosystems.

A common cause of water quality deterioration in aquaculture systems is the excessive proliferation of algal biomass. Methods of management of this include the application of chemicals, water exchange and manual removal. Copper sulfate is one of the most commonly applied chemical for the purpose. Other chemicals reported include the compound 3-(4-tolylsulfonyl) acrylonitrile (Gutman, 1982), N-acetonylbenzamides compounds (Luis and Hamilton, 1999) and α-substituted amines and α-amino acids (Albert, 1982). Another method has been used wherein the water is passed through a magnetic field, which is normal to the direction of flow of the water (Alexander, 1977). Barley straw decomposing in water is found to control the growth of algae in both laboratory and field trials (Ridge and Barrett, 1992). Treatment with barley straw reduces the cyanobacterial dominance in the aquatic ecosystems (Everall and Lees, 1996). Tellimagrandin II present in the aquatic macrophyte *Myriophyllum spicatum* was found to be inhibitory to the growth of cyanobacteria (Leu et al., 2002).

Pathogenic bacteria are another major cause of decline in water quality as well as causative agents of many diseases in aquaculture. Sanitizers and disinfectants have been employed to control the pathogens, but their application is limited in aquaculture due to the possible toxic and residual effects. Different probiotic strains have been used in aquaculture for the control of diseases and improvement of water quality (Keeton and Williams, 2005; Kruse, 2008). Lactic acid bacteria were found to act as a microbial barrier against the pathogenic Vibrio (Gatesoupe, 1994). A strain of Pseudoalteromonas improved the survival of juvenile Pacific oysters exposed to pathogenic Vibrio sp. (Elston, 2008).

Chemicals such as copper sulfate, N-acetonylbenzamides compounds and a-substituted amines have been used to prevent excessive cyanobacterial proliferation. Other methods included the use of water exchange and manual removal. To reduce the resultant deterioration of water quality, methods such as use of aerators, use of ammonia binding compounds etc. have been tried. Chemicals have drawbacks such as toxicity and residual effects. Water exchange has been observed not to be commercially viable and manual removal is labor intensive. The above mentioned methods have also been found to give short term solution and the proliferation of cyanobacteria reoccurs within few days. Methods to reduce the resultant deterioration in water quality do not give long-lasting effects since they do not address and solve the problem directly.

Studies on improving the aquaculture water quality have been conducted by Claude E. Boyd and Craig S. Tucker, authors of the book, Pond Aquaculture Water Quality Management, which reviews the different methods followed to improve the water quality. The studies have shown harmful effects of use of chemicals such as simazine, including reduction in dissolved oxygen levels and mortality of the cultured species. Several researchers including Ridge, I, Pillinger, M., Everall, N. C. and Lees, D. R have evaluated the application of barley straw for the control of cyanobacteria. Probiotics have been studied extensively for the control of pathogenic bacterial species and for the improvement of water quality by researchers including Laurent Verschuere, Gatesoupe, F. J. and Austin, B.

Methods to improve water quality in aquatic ecosystems including aquaculture ponds consists of use of biofilters, aerators, use of silicates, ammonia binding agents, probiotics, algae control agents, water exchange etc. Application of silicates is reported to improve the physical quality of water (Conner et al., 1977). Physical and biological filtration systems are used alone or in combination with sedimentation systems for improving the physical, chemical and microbiological quality of water in aquaculture (Chang, 2005). Probiotic bacterial strains are used to inhibit or prevent the growth or pathogenic bacteria (Elston et al., 2006; Verschuere, 2000) thereby improving the microbiological quality of water. Few of the probiotic strains of bacteria also improve the chemical quality of water also. Gram-positive Bacillus spp. are more efficient in converting organic matter back to $CO_2$ than are gram-negative bacteria (Stanier, 1963), and hence pose the potential for use as probiotics. However, several studies utilizing one or more bacterial species such as Bacillus, Nitrobacter, Pseudomonas, Enterobacter, etc. (Lin, 1995; Maeda and Liao, 1994) could not confirm this effect in aquaculture.

The herb *Quercus infectoria*, commonly called Oak gall, produces galls in response to infestation by an insect (*Diplolepis gallae tinctoriae*, or *Cynips quercufolii*) for the purpose of depositing its egg. A small tumor soon follows the puncture, and forms a very dense mass about the egg. The egg hatches into the fly while in these tumors, eating its way by a small opening. The galls are known for its medicinal properties, used as astringents and anti-diarrheal and are rich in phenolic compounds. However there are no studies reported on the application of *Quercus infectoria* nut galls on improving water quality. The herbal source is being used in medicinal preparations and is safe and environment friendly. It is cost-effective and showed long term effects in the laboratory studies. Besides, it could also lead to other desirable effects such as reducing pathogenic microbes and a resultant overall improvement of water quality.

SUMMARY OF THE INVENTION

The present invention relates to the development of a herbal based product for improving the water quality in aquatic ecosystems, including aquaculture farms. A method was developed at lab to prepare an alkaline extract using the *Quercus infectoria* nut galls.

Algal blooms deteriorate the water quality, reduce growth rate of aquaculture species and leads to mortality, causing significant economic losses to the farmers. At present there is no environment friendly and practical solution to the problem of excessive proliferation of cyanobacteria and pathogenic bacterial species in aquaculture systems and hence there is a market demand for such a product. There is a need for a safe and effective product. The herbal powder/extracts of the present invention are applied to the water body to be treated, to maintain the population of cyanobacteria at desirable levels and reducing the pathogen counts, enhancing profit to fish farmers. The product can also be used in aquarium systems for improving the water quality and clarity.

Use of a chemical process involving use of alkali and hydrogen peroxide for the production an extract from *Quercus infectoria* nutgalls for the purpose mentioned is novel. Nutgalls from the herb *Quercus infectoria*, though well studied for its medicinal properties, have not been reported in application in water for the improvement of water quality. For the same purpose, different chemicals, plant parts/extracts have been mentioned in literature, but none has reported the application of *Quercus infectoria* nut galls. The application of *Quercus infectoria* nutgalls for the control of cyanobacteria have not been reported before. Similarly, the application of *Quercus infectoria* nutgalls against water-borne pathogens or other water-borne microorganisms has not been evaluated before.

The invention includes a method of preparation of a chemical extract from *Quercus infectoria* nutgalls using alkali and an oxidizing agent for the release of phytochemicals desirable for improving the water quality in aquatic ecosystems. This method has been practiced and has been proven to be effective in reducing excessive proliferation of cyanobacteria in pure culture. Further study on the phytochemicals in the extract will include identifying broad groups of compounds and quantitative profiling towards the identification of active ingredient/s.

The invention also includes the application of *Quercus infectoria* nutgall powder/water extract/alkaline extract for reducing excessive proliferation of cyanobacteria and algae, thereby improving water quality in aquatic ecosystems.

Also included in the invention is the application of *Quercus infectoria* nutgall powder/water extract/alkaline extract for inhibiting the growth of pathogenic bacterial species in aquaculture thereby preventing mortality and infection in aquaculture species.

The invention also comprises the application of *Quercus infectoria* nutgall powder/water extract/alkaline extract for inhibiting the growth of pathogenic bacterial species in aquatic ecosystems thereby improving the water quality.

DETAILED DESCRIPTION OF PREFERRED EMBODIMENTS

*Quercus infectoria* nutgalls have been found to have a number of medicinal properties including anti-diarrheal, anti-diabetic, anti-inflammatory and astringent activity. They have been found to have antimicrobial properties against gram positive and gram negative bacteria (Basri and Fan, 2005; Fatima et al., 2001). However *Quercus infectoria* nutgalls have not been studied for their activity against excessive proliferation of cyanobacteria and pathogenic bacteria in aquatic ecosystems.

*Quercus infectoria* nut galls are used in medicinal preparations and are found to have antimicrobial properties based on the studies conducted against few bacterial species. However it does not ensure it to be inhibitory to cyanobacterial proliferation. Cyanobacteria are prokaryotes, containing chlorophyll-a and differ from other photosynthetic bacteria by the presence of phycobiliproteins. They were traditionally classified as a group of algae and are morphologically and developmentally one of the most diverse groups of prokaryotes. They range from simple unicellular forms to complex filamentous forms that possess a variety of highly differentiated cell types. They have complex cell wall structure, combining that of gram-negative and gram-positive bacteria, which is impermeable to most antibiotics. A majority of the cyanobacteria are resistant to antibiotics and are normally controlled by the use of chemicals such as copper sulfate.

The extract/powder from *Quercus infectoria* nut galls has not been studied against pathogens in water. The alkaline extraction process described also does not relate to any of the previous methods used for the release of phytochemicals for biological activity. Preferred alkali compounds are carbonates, bicarbonates and hydroxides of sodium and potassium, with the reaction varying in speed depending on the alkali compound used and its solubility. The ratio of nutgalls to alkali can be adjusted during the extraction process to have a pH range of preferably between 9-12.5 at the start of the process which will be expected to be reduced to about between 8-11 at the completion of the process. Metasilicates are preferably included in the formulation at between about 5-10%.

EXAMPLE 1

A method was developed in the lab to prepare an alkaline extract using the Quercus infectoria nut galls.

*Quercus infectoria* nut galls were broken into small pieces using a steel rod and were ground to a fine powder in a domestic mixer grinder. The powder was free-flowing, cream colored and had a characteristic smell.

For the production of an alkaline extract, 20 g of powder was mixed in 100 ml of water, 1 g NaOH and 0.1 g $Na_2SO_4$ were added and the slurry was heated at 70° C. for 30 minutes in a water bath. One g $H_2O_2$ was added to the slurry after 30 minutes and the mixture was heated for another 30 minutes. The slurry was allowed to cool and was centrifuged at 4000 rpm for 10 minutes. The supernatant was collected. The centrifugation step was repeated thrice to get a clear supernatant.

For comparison purposes, a water extract of the nut galls was prepared by adding the powder to water in a 1:5 ratio, keeping at room temperature for one hour and centrifuging as before to obtain a clear supernatant.

To test the two extracts, culture flasks were prepared using Media MN (Marine Nutrient medium). The media was prepared by combining the list of ingredients in Table 1 and the pH was adjusted to 8.3, followed by autoclaving at 121° C., 15 lbs, for 15 minutes to sterilize the media. The media was allowed to cool to ambient temperature prior to use.

TABLE 1

Marine Nutrient medium (Media MN):

| Ingredient | grams/liter |
|---|---|
| $NaNO_3$ | 0.75 |
| $K_2HPO_4$ | 0.02 |
| $MgSO_4 \cdot 7H_2O$ | 0.038 |
| $CaCl_2 \cdot 2H_2O$ | 0.018 |
| Citric acid | 0.003 |
| Ferric ammonium citrate | 0.003 |
| EDTA (disodium salt) | 0.0005 |
| $Na_2CO_3$ | 0.02 |
| Trace metal mix (see Table 2) | 1 ml |
| Seawater | 750 ml |
| Deionized water | To 1 liter |

The trace metal mix mentioned in Table 1 was prepared using the list of ingredients as given in Table 2.

TABLE 2

Trace metal mix

| Ingredient | grams/liter |
|---|---|
| $H_3BO_3$ | 2.86 |
| $MnCl_2 \cdot 4H_2O$ | 1.81 |
| $ZnSO_4 \cdot 7H_2O$ | 0.222 |
| $Na_2MoO_4 \cdot 2H_2O$ | 0.39 |
| $CuSO_4 \cdot 5H_2O$ | 0.079 |
| $Co(NO_3)_2 \cdot 6H_2O$ | 0.049 |
| Deionized water | To 1 liter |

Twenty (20) ml of the Medium MN was placed in 150 ml Erlenmeyer flasks and inoculated with a pure culture of *Synecocystis* (0.5 ml). Ten µl of the water extract was added to one set of three flasks and 10 µl of the alkaline extract was added to another set of three flasks. Another set of three flasks were kept as control. Samples were drawn on days 1, 3 and 7 and were analyzed for cyanobacterial counts using a hemocytometer.

Figure 1:
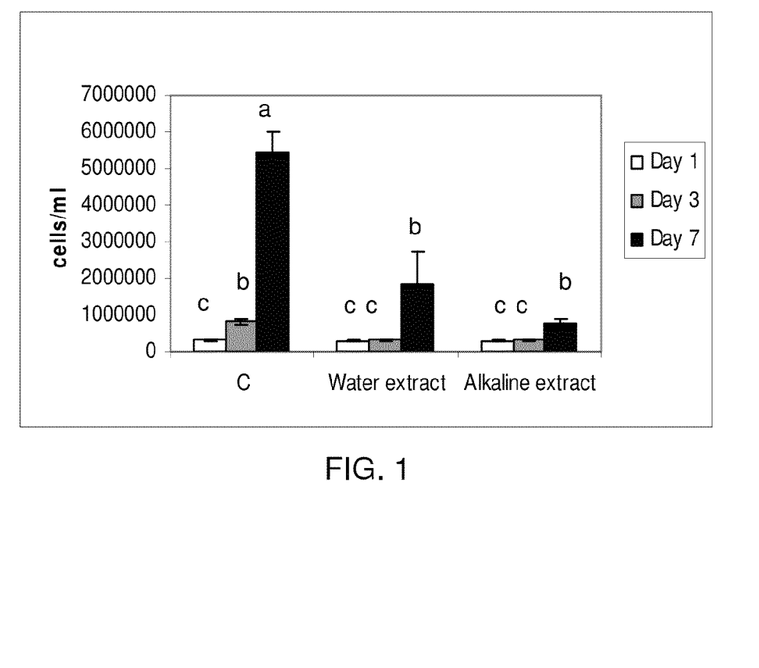
FIG. 1 is a chart of the effect of *Quercus infectoria* nut galls alkali and water extract on cyanobacteria *Synecocystis* sp. in pure culture.
Figure 2:
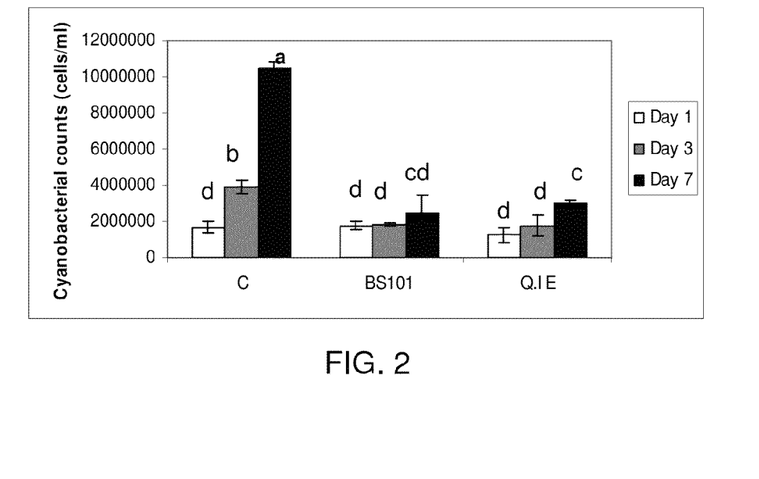
FIG. 2 is a chart of the effect of *Quercus infectoria* extract prepared at lab and that procured from external supplier on the growth of cyanobacteria *Synecosytis* sp.

It was found that the alkaline extract and the water extract had different but not significantly different efficacy (a chart of the effect of the alkaline extract compared to control is shown in FIG. 1), indicating the that the nut gall powder could simply be added into the water of aquaculture ponds to have its effect on the cyanobacteria present.

EXAMPLE 2

Another experiment was run to compare the efficacy of the nut gall extract prepared in the lab with that of a commercially available nut gall extract obtained from Ecotech Technologies Pvt. Ltd. (Mumbai, India), which was identified by the supplier as a water extract which had been concentrated five times.

The experiment described above was repeated with the nut gall (coded as BS 101) extract prepared at lab and the commercial extract added at equal quantities to the pure cultures of *Synecocystis* in Media MN. The effect on cyanobacterial growth was studied for a period of 7 days by taking the cell counts. The commercial extract and BS 101 extract prepared at lab were found to have equal efficacy in reducing the counts of cyanobacteria. Since it is difficult to ensure consistent quality in the extract procured from a third party and also since there could be adulteration of extract, it was decided to progress on further studies with the BS 101 powder/extract prepared at the lab itself.

EXAMPLE 3

Since the product BS 101 was found to inhibit the growth of diatoms, a few formulations were made containing diatom growth enhancers to nullify this effect. This was important since diatoms are beneficial in shrimp ponds as live feed for the post larvae and juveniles of shrimps. Since silicates are integral parts of diatom cell wall, supplementation of sodium silicate can enhance the growth of diatoms. Hence sodium metasilicate was included in the formulation. The combination of cyanobacterial inhibition with diatom growth enhancement characteristics makes this formulation unique.

EXAMPLE 4

The studies conducted at the lab showed that the alkaline extract, as well as a water extract, from *Quercus infectoria* nut galls reduces the proliferation of the cyanobacteria *Synecocystis* sp. in pure culture. *Synecocystis* is a dominant cyanobacterium in aquatic ecosystems especially in brackish water aquaculture systems and the excessive blooming of cyanobacteria causes water quality deterioration including pH fluctuations, reduction in dissolved oxygen levels and release of toxic gases. They also affect the physical quality of water by increasing turbidity. By maintaining the cyanobacterial population at desirable levels, the extract from *Quercus infectoria* galls would be able to enhance the water quality in aquatic ecosystems. The effectiveness of the product in reducing excessive proliferation of other cyanobacterial and algal species and also in presence of diverse aquatic flora and fauna is under investigation. These experiments would also cover the use of powder from *Quercus infectoria* nutgalls in place of an extract for the purpose mentioned above.

Another aspect of the invention is related to the application of an alkaline or water extract of *Quercus infectoria* nutgalls for improving the microbiological status of water by inhibiting the growth of pathogens/opportunistic pathogens in water. Cyanobacteria are not considered to be pathogenic per se in nature and many species are desirable at optimum populations for the balance of the aquatic ecosystems. Pathogenic bacterial species in aquaculture systems infect the cultured species, reducing their growth rate and causing mortality. In addition, many of them compete with beneficial bacteria and inhibit their growth, thereby indirectly affecting the nutrient recycling processes leading to deterioration of water quality.

EXAMPLE 5

An experiment was run to determine the composition of the nut gall powder. *Quercus infectoria* nut gall powder (20 g) was soaked in 100 ml water for one hour. The clear supernatant obtained after centrifugation was used for phytochemical analysis. Qualitative analysis was done to test the presence of tannins, coumarins, quinones and saponins. An equal volume of the supernatant was added to a 1:1 aqueous solution of ferric chloride to obtain a blue-black precipitate showing the presence of tannins. Two ml of the supernatant was mixed with 5 ml of distilled water. The mixture was subjected to vigorous stifling which developed frothing showing the presence of saponins. Two ml of the supernatant were mixed with 2 ml of concentrated $H_2SO_4$ and which obtained a red color indicating the presence of quinones. Two ml of the supernatant were mixed with 2 ml of 10% NaOH and which obtained a yellow color indicating the presence of coumarins. Use of the Folin's-Ciocalteau method of total polyphenol estimation showed 1.1 g total polyphenols released per 100 g sample when extracted for one hour in water.

The alkaline and water extract from *Quercus infectoria* gall were thus found to have high amount of polyphenols including tannins, coumarins, quinones and saponins. The phytochemicals from *Quercus infectoria* are reported to have antimicrobial properties, although they have not been investigated against pathogenic bacteria in water.

Preliminary qualitative phytochemical analysis showed the presence of saponins, tannins, coumarins and quinones. The specific components in each of these broad categories of compounds, is being studied to identify the compound/s responsible for the activity(ies).

EXAMPLE 6

In other experiments, the effect of the nut gall extract on the growth of diatoms was tested. *Quercus infectoria* extract was prepared as described previously. Media MN with sodium silicate (0.03 g/litre) was prepared for growth of diatoms and was transferred to sterile conical flasks under aseptic conditions. To the media equal volume of pure culture of the diatom *Chaetoceros* sp. was added as inoculum. Ten µl of the extract was added to treatment flasks and triplicate flasks were maintained for the control as well. The flasks were incubated for 7 days and the growth of diatoms was studied by taking the cell counts at regular intervals. The extract was found to have an effect on the growth of diatoms as was shown by the cell counts on day 3 and day 7.

EXAMPLE 7

Figure 3:
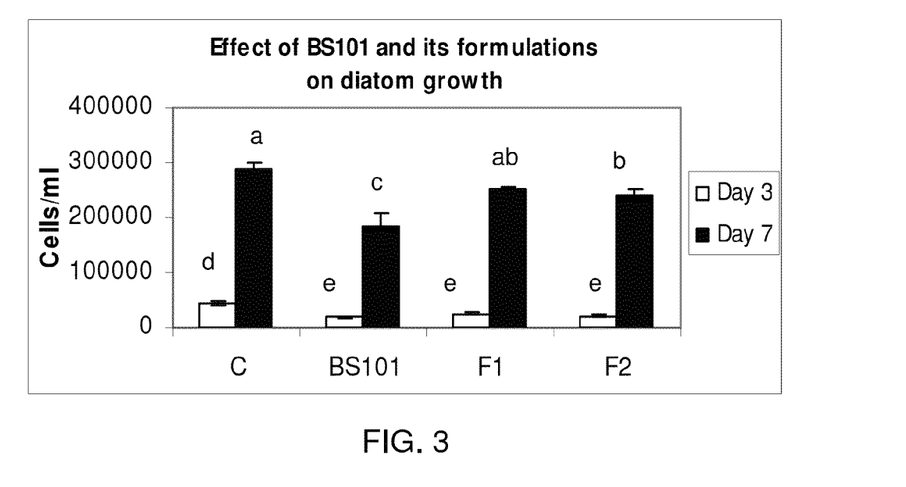
FIG. 3 is a chart of the effect of *Quercus infectoria* nut galls (BS 101) and its formulations on the growth of the diatom *Chaetoceros* sp.

The formulations were studies for their effect on diatom growth as compared to pure *Quercus infectoria* nutgall powder (BS 101) using pure cultures of the diatom Chaetoceros sp. The culture conditions were same as described previously. For the treatment groups, formulation F1 or F2 or BS101 were added to the culture flasks. Diatom counts were taken using a hemocytometer. BS 101 was found to reduce the growth of diatoms significantly. The formulations had lesser effect on diatom growth (p<0.05). Formulation F1 was comparable to the control in terms of the diatom growth. The results of the study are shown in FIG. 3

EXAMPLE 8

In another experiment, the effect of the nut gall extract on the growth of Vibrio spp. isolated from shrimp pond water was tested. The extract was prepared by adding 20 g of nut gall powder into 100 ml of water, soaking for one hour followed by centrifugation. Chloramphenicol (25 µg/ml) was taken as positive control. Vibrio isolation agar was prepared and the agar plates were cooled to room temperature. Sterile disk was placed in the centre of agar plate, after inoculating Vibrio spp. using a sterile cotton swab. 10 µl of extract/antibiotic was added to the disk and incubated at 37° C. in an incubator. After incubation the plates were observed for the clear zone of inhibition. The BS 101 extract showed 11 mm zone of inhibition as compared to 13 mm zone of inhibition by the antibiotic.

EXAMPLE 9

An experiment was conducted to determine the LC-50 of the nut gall extract on the aquaculture species tiger shrimp (*Penaeus monodon*) to ensure the safety of the *Quercus infectoria* nutgalls (BS101). The 96-hour LC-50 was estimated in tiger shrimp post larvae (PL-20). The study was done with 6 dosages of the product 0, 0.5, 5, 50, 100, 500 and 1000 µg/ml, each in triplicates. The experiment was conducted in 5 liter tubs with 8 post larvae in each tub. There was no water exchange during the experiment period. Aeration was done continuously and the waste was siphoned out on a daily basis. The PL were fed with PL feed during the experiment period. The number of survivors was recorded daily and the 96-hour data was analyzed using SPSS statistical software to arrive at the LC 50 value. The value was estimated to be 43.124 µg. However since the range of dosages were broad, the study was repeated with a narrower range (0-100 µg/ml) to get a better line of fit. The value was estimated to be 63.196 ppm whereas at a dosage of 3 kg/acre the application comes to about $\frac{1}{90}^{th}$ of this. Hence the experiment proved the safety of the product for application in shrimp culture.

EXAMPLE 10

Figure 4:
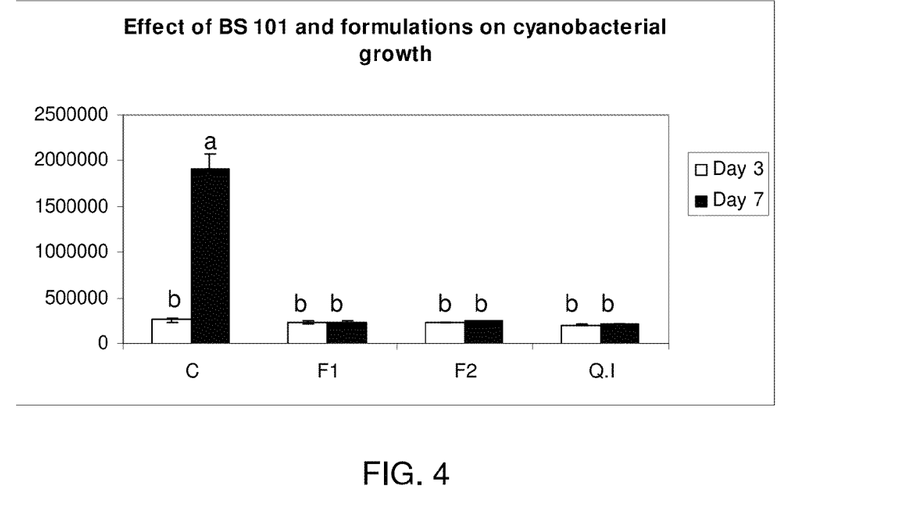
FIG. 4 is a chart of the effect of *Quercus infectoria* nut galls (BS 101) and its formulations on the growth of the cyanobacterium *Synecocystis* sp.

An experiment was conducted to determine the effect of the nut gall powder and the formulations prepared on the growth of cyanobacteria. The formulations prepared as per Example 3 were studied to check whether the formulations which reduced the diatom inhibitory activity have affected the cyanobacterial inhibitory activity. The cyanobacterial inhibitory effect was studied on *Synecocystis* spp. inoculated in equal amounts into flasks having the media MN. 10 mg each of the *Quercus infectoria* powder, formulations F1 or formulation F2 were added to triplicate treatment flasks. A set of triplicate flasks were maintained for the control as well. The flasks were incubated for seven days and observed for cyanobacterial growth by measuring the cell counts. It was observed that all the formulations were equally effective as BS 101 powder in reducing the counts of cyanobacteria compared to control. The results are shown in FIG. 4.

EXAMPLE 11

Figure 5:
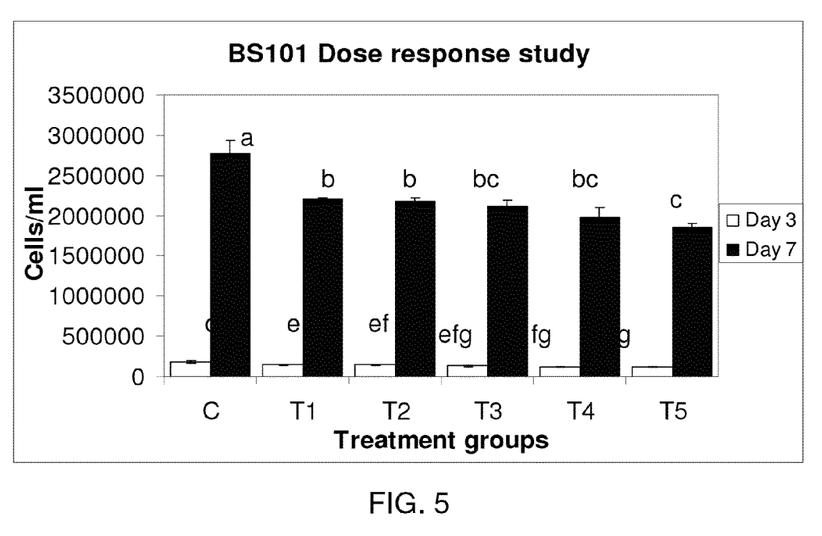
FIG. 5 is a chart of the dose response study of Formulation F1 on the growth of *Cyanobacteria*.

An experiment was conducted to determine the dose response effect of the selected formulation F1 on the growth of cyanobacteria. The cyanobacterial inhibitory effect was studied on *Synecocystis* sp. as per the method described in Example 10. For the treatment groups, formulation F1 was added at dosages of 0.6 mg/600 ml, 0.9 mg/600 ml, 1.2 mg/600 ml, 1.5 mg/600 ml, and 1.8 mg/600 ml. The cyanobacterial biomass of the groups was assessed on Day 3 and Day 7 and were compared between the treatment groups and also with the control. All the dosage groups were effective in bringing down the cyanobacteroal counts compared to control. The results are as shown in FIG. 5.

EXAMPLE 12

The mechanism of action of Formulation F1 was evaluated in unicellular and filamentous cyanobacterial species. The studies were conducted at the National Facility for Marine Cyanobacteria. The experiment specifically evaluated the effect of Formulation F1 on induction of oxidative stress, by estimating the enzymes and metabolites associated with oxidative stress metabolism, after incubation with Formulation F1. The enzymes involved in cellular anti-oxidant defence mechanism, namely superoxide dismutase, catalase, glutathione peroxidase and glutathione reductase were estimated. The end products of non-enzymatic defence system and lipid peroxidation namely glutathione and malonaldehyde respectively, were also estimated at different intervals after exposure to Formulation F1.

It was found that Formulation F1 induces production of reactive oxygen species (ROS) in cyanobacteria and activates cellular defence mechanisms in cyanobacteria as indicated by the enzymes and metabolites of ROS production. It was found to induce the production of ROS as measured by the shift in the enzyme activities on exposure to Formulation F1 as compared to control. The malonaldehyde levels showed an increase (p<0.05) in Formulation F1 treated samples and glutathione levels showed a decrease (p<0.05) indicative of oxidative stress. *Cyanobacteria* are highly sensitive to ROS unlike other algae. ROS stimulates photodamage by inhibiting the repair to photosystem II. The oxidative stress and resultant macromolecular damage leads to inhibition of photosynthesis and cell proliferation.

EXAMPLE 13

Farm trials were conducted at commercial fish and shrimp farms at various locations in India viz. Bhimavaram, Nellore, Ongole (AP), Marakkanam, Sirkazhi (Tamilnadu), Balasore (Orissa). The farms varied with regard to water source, plankton biodiversity, species of culture and salinity ranges (0-40 ppt) and the trials were aimed to confirm the efficacy of the product in the dynamic pond environment, throughout the culture period. The trials have given promising results in terms of reduction in Cyanobacterial counts, maintenance of water quality, total shrimp production and survival rates as compared to control ponds not receiving Cyano CURB treatment. Given below are the details of one such experiment, conducted at a shrimp farm located at Marakkanam, Tamilnadu, India. The species under culture was tiger shrimp, *Penaeus monodon*. The product was applied at 1 kg/acre in the treatment pond.

The parameters evaluated during the trial included chlorophyll concentration, cyanobacterial counts, water quality parameters and performance parameters. For measurement of chlorophyll concentration, 100 ml of thoroughly mixed pond water collected from four corners and centre of the pond during morning hours (8-8.30 am) was filtered through a glass microfiber filter (Whatman GF/C). The dry biomass retained in the filter (pore size 1.2 µm) was extracted using methanol (10 ml). It was allowed to stand overnight at 4° C. and incubated in dark by covering the tubes with aluminum foil. The contents were centrifuged (500 g, 10 min) and optical density of the supernatant was measured at 665 nm. Chlorophyll—a content was calculated using the formula:

Chlorophyll—$a(\mu g/1)=O.D\times12.63\times$(Volume of methanol×1000/ volume of sample).

Water quality parameters viz. dissolved oxygen, pH, ammonia and nitrate were measured by using commercial test kits (AA Biotech, India). Shrimp feed intake was recorded on a daily basis. Check tray was observed for any left over feed and daily ration was determined accordingly. Shrimps were observed on a weekly basis for weight gain through cast netting. Observations on any signs of disease, moulting pattern, fungal attachment etc. were also recorded. Weight at final harvest was measured.

Figure 6:
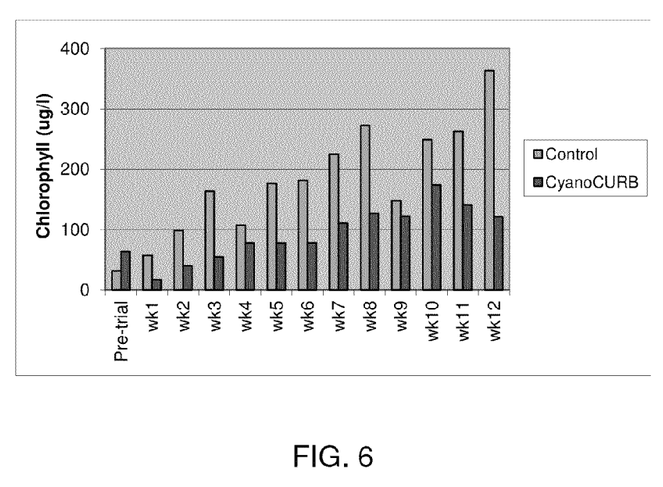
FIG. 6 is a chart of the effect of Cyano CURB on total algal counts during the trial of Example 13.

There was considerable reduction in chlorophyll levels in the treated pond throughout the trial period, indicating lower algal biomass as compared to the control pond (FIG. 6).

The reduction in chlorophyll levels was found to correlate with a reduction in cyanobacterial density in the treated pond as compared to control.

Dissolved oxygen and pH levels were not affected by product application and algal inhibition. Nitrate and ammonia levels were within normal levels in both ponds. There was also a visible difference in the appearance and color between the ponds. The control pond had dark green color indicative of a bloom development by 45 days of culture, which increased on subsequent days. The Formulation F1 treated pond maintained the characteristic golden yellowish color desirable in shrimp ponds.

Application of Formulation F1 improved the yield and survival of shrimp leading to better return on investment (Table 3).

TABLE 3

Effect of Formulation F1 on the performance parameters in the trial pond compared to control

| Trial 1 | Control | Treatment |
| --- | --- | --- |
| Pond area | 0.7 ha | 0.8 ha |
| Stocking density (no.) | 110,000 | 138,448 |
| DOC at harvest | 130 | 143 |
| Biomass (kg) | 2750 | 3650 |
| Survival (%) | 89 | 91 |
| Total cost of production (Rs.) | 380,185 | 477,999 |
| Cost of production/kg shrimp (Rs.) | 137 | 128 |

EXAMPLE 14

The product was tested at a fish farm at Bhimavaram, Andhrapradesh, India and two trials were done at shrimp ponds, Nellore, Andhrapradesh, India.

Trial 1

The trial was conducted at a fish pond located at Bhimavaram. The pond of 0.5 acre with the water depth of 1.2 m was used for the study. The pond harbored the culture of catfish *Anabas testudineus* with the stocking density of 20,000. The days of culture at the initiation of the trial were 4 months. The product was supplemented at a concentration of 2 kg/acre. The product was applied by mixing with water and spraying uniformly throughout the pond.

Trial 2

The trial was conducted at Nellore, Andhrapradesh, India. The pond was of 3 acre area and water depth of 1 m. The pond harbored the 90 days old culture of *P. monodon*. The salinity was observed to be 5ppt. The product was supplemented at the concentration of 2 kg/acre.

Trial 3

This trial was also conducted at a shrimp pond located at Nellore. The pond was of 2.5 acre area and water depth of 1m. The species of culture was *P. monodon* with stocking density of 50,000. The product application was done at 90 days of culture. The source of water for the pond was canal water mixed with bore water. The salinity was observed to be 5 ppt. The product was supplemented at 1 kg/acre.

Parameters Analyzed:

Total algal counts were estimated based on chlorophyll estimation on water samples collected on 0 day (day of product application), 7th day and 14th day of the trial period.

Cyanobacterial density was observed on selective plates inoculated with 0.5 ml of pond water collected at regular intervals during the trial period. Media MN with cycloheximide (for preventing the growth of eukaryotes) was used as the selective media. Commercial kits were used to estimate the water quality parameters namely pH, dissolved oxygen, nitrate and ammonia measurements.

Results

Figure 7:
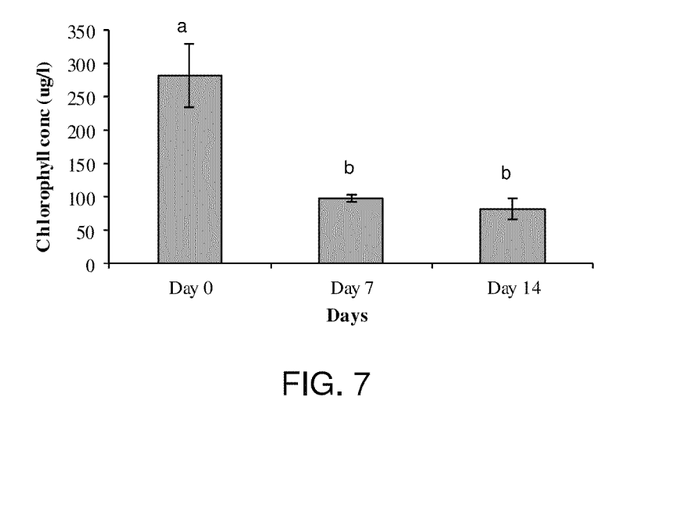
FIG. 7 is a chart of the difference in chlorophyll content of the pond water in Example 14 before and after Formulation F1 application.

Trial 1: There was significant reduction (p<0.05) in algal counts observed after one week of product application and the reduced levels were maintained through the second week as well (FIG. 7). The pH was very high before product application and reduced to normal levels after the treatment. There was slight increase in the ammonia levels after two weeks of the trial, which indicates the cyanobacterial reduction and subsequent decomposition in the pond. The product application did not reduce the dissolved oxygen levels below 3 ppm throughout the trial period (Table4). The density of cyanobacterial growth in the selective plates clearly showed considerable reduction in algal counts before and after the product application. Common algicides such as copper sulfate bring in a sudden reduction in algal counts which causes a drastic deterioration of water quality. Formulation F1 reduced cyanobacterial counts gradually over a period of seven days without affecting the water quality parameters.

TABLE 4

Variations in water quality of the pond before and after Formulation F1 application

| Days | pH | Ammonia (ppm) | Nitrate (ppm) | Dissolved oxygen (ppm) |
|---|---|---|---|---|
| 0 | 9.5 | <0.1 | <0.5 | 3.25 |
| 7 | 8.8 | <0.1 | <0.5 | 5.5 |
| 14 | 8.8 | 0.25 | <0.5 | 3.25 |

Trial 2: The farm had a loose shell problem at the beginning of study itself, which was indicative of heavy cyanobacterial bloom. The initial chlorophyll content was observed to be 454.68 ug/l however the algae growth was reduced to 40% than the initial state after 10 days of product application. The shrimps were observed to come to the periphery which is indicative of stress and difficulty in respiration. The dissolved oxygen, nitrate and pH of the water were not affected (Table 5), whereas ammonia levels were observed to be high (1 ppm). The shrimps are sensitive to ammonia levels higher than 0.25 ppm, which could be the reason for difficulty in respiration and stress. However to rule out any effect of product application on stress to shrimps, it was decided to observe any symptoms of stress on a regular basis after product application in subsequent trial. Since the culture had already reached an average size of 20 g, the farmer decided to harvest and hence the trial was discontinued.

The trial gave insight in to the importance of using Formulation F1 as a preventive measure rather than for treatment in a cyanobacterial bloom condition. Under a severe bloom condition the water quality deteriorates, the animals would be in stress and prone to infections, and it would be difficult to achieve the expected performance levels even after controlling the bloom condition by using Formulation F1.

TABLE 5

Variation in water quality of the pond before and after Formulation F1 application

| Days | Dissolved Oxygen (ppm) | Nitrate (ppm) | pH |
|---|---|---|---|
| 0 | 7.8 | <5 | 8.4 |
| 14 | 7.8 | <5 | 7.4 |

Figure 8:
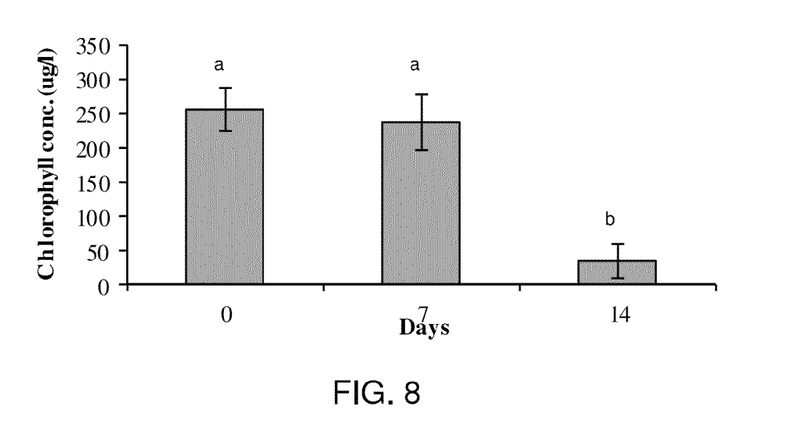
FIG. 8 is a chart of the difference in chlorophyll content of the pond water before and after Formulation F1 application in Example 14.

Trial 3: In this trial the product dosage was reduced to 1kg/acre. FIG. 8 shows the reduction in algal counts during the trial period. There was a gradual reduction in algal counts until 7th day of product application and the counts reduced significantly ($p<0.05$) when analyzed on the 14th day. The bloom disappearance was clearly visible on the 14th day observation. There was considerable improvement in water quality after product addition and subsequent algal inhibition (Table 6). The animals were observed to be healthy and there were no signs of stress on application of product. Supplementation of product at a dosage of 1 kg/acre was found to be sufficient to cause significant reduction in algal counts.

TABLE 6

Variations in water quality of the pond before and after Formulation F1 application.

| Days | Dissolved oxygen (ppm) | pH | Nitrate (ppm) |
|---|---|---|---|
| 0 | 2.6 ± 0.1 | 10.91 ± 0.014 | <5 |
| 7 | 3.58 ± 0.45 | 10.46 ± 0.36 | <5 |
| 14 | 6.15 ± 0.49 | 9.7 ± 0.03 | <5 |

Values are mean ± SD. n = 3

The reduction in total algal counts was found to correlate with the reduction in cyanobacterial density as observed on the specific cyanobacterial plates. There was also a corresponding improvement in pond appearance and color, changing from the dark green bloom color to yellowish green, which is desirable in shrimp ponds.

CONCLUSION

The trials showed a reduction in algal counts as measured by the chlorophyll concentrations. The effect on cyanobacterial growth was also evident from the reduction in cyanobacterial density observed in selective plates inoculated with pond water samples at regular intervals after product application.

Application of Formulation F1 did not affect the pond water quality, unlike algicides which cause a sudden algal crash and a resultant deterioration of water quality. Improvement of water quality was observed as a result of reduction in cyanobacterial population.

The foregoing description and drawings comprise illustrative embodiments of the present inventions. The foregoing embodiments and the methods described herein may vary based on the ability, experience, and preference of those skilled in the art. Merely listing the steps of the method in a certain order does not constitute any limitation on the order of the steps of the method. The foregoing description and drawings merely explain and illustrate the invention, and the invention is not limited thereto, except insofar as the claims are so limited. Those skilled in the art that have the disclosure before them will be able to make modifications and variations therein without departing from the scope of the invention.

We claim:

1. A method of treating excessive proliferation of cyanobacteria and algae in an aquatic ecosystem in need thereof consisting essentially of adding to the aquatic ecosystem an effective amount of *Quercus infectoria* nut gall powder which thereby reduces the amount of cyanobacteria and algae in the aquatic ecosystem and thereby improves the physical, chemical and microbiological quality of the water in the aquatic ecosystem.

2. A method of treating excessive proliferation of cyanobacteria and algae in an aquatic ecosystem in need thereof consisting essentially of adding to the aquatic ecosystem an effective amount of *Quercus infectoria* nut gall extract which thereby reduces the amount of cyanobacteria and algae in the aquatic ecosystem and thereby improves the physical, chemical and microbiological quality of the water in the aquatic ecosystem.

* * * * *